United States Patent [19]

Shimoyama

[11] Patent Number: 5,056,531
[45] Date of Patent: Oct. 15, 1991

[54] ELECTRODE STRUCTURE FOR HIGH FREQUENCY HYPERTHERMIA DEVICE

[75] Inventor: Jun Shimoyama, Kyoto, Japan

[73] Assignee: Omron Tateisi Electronics Co., Kyoto, Japan

[21] Appl. No.: 427,876

[22] Filed: Oct. 30, 1989

[30] Foreign Application Priority Data

Nov. 7, 1988 [JP] Japan ................. 63-145320
Nov. 7, 1988 [JP] Japan ................. 63-280684

[51] Int. Cl.$^5$ ................................. A61N 1/06
[52] U.S. Cl. ............................. 128/784; 128/800; 128/804; 128/400; 128/401
[58] Field of Search ............ 128/804, 784, 800, 400, 128/401; 604/22

[56] References Cited

U.S. PATENT DOCUMENTS 3,991,770 11/1976 LeVeen .................. 128/800 X
4,140,130 2/1979 Storm .................... 128/804 X
4,846,790 7/1989 Hornlein et al. ............. 604/22
4,887,614 12/1989 Shirakami et al. ........... 128/804 X

FOREIGN PATENT DOCUMENTS

0251746 1/1988 European Pat. Off. ......... 128/804

Primary Examiner—Lee S. Cohen
Attorney, Agent, or Firm—Fish & Richardson

[57] ABSTRACT

In an electrode structure for a high frequency hyperthermia device, an electrode unit incorporating an electrode is provided at the front end of a supporting arm, and an inflatable insulated bag is provided on one side of the electrode unit, whereby the electrode unit is snugly brought into contact with the diseased part as the bag is inflated, and a cooling solution containing bag is detachably mounted on the other side of the electrode unit, whereby the solution containing bag can be readily replaced with a new one when broken, and the solution containing bag most suitable for treatment of the diseased part can be readily engaged with the electrode unit.

5 Claims, 9 Drawing Sheets

ELECTRODE STRUCTURE FOR HIGH FREQUENCY HYPERTHERMIA DEVICE

BACKGROUND OF THE INVENTION

This invention relates to the electrode structure of a high frequency hyperthermia device which is inserted into an oral cavity to treat a cancer tissue or the like in its narrow part by heating it with high frequency electric field.

Figure 8A:
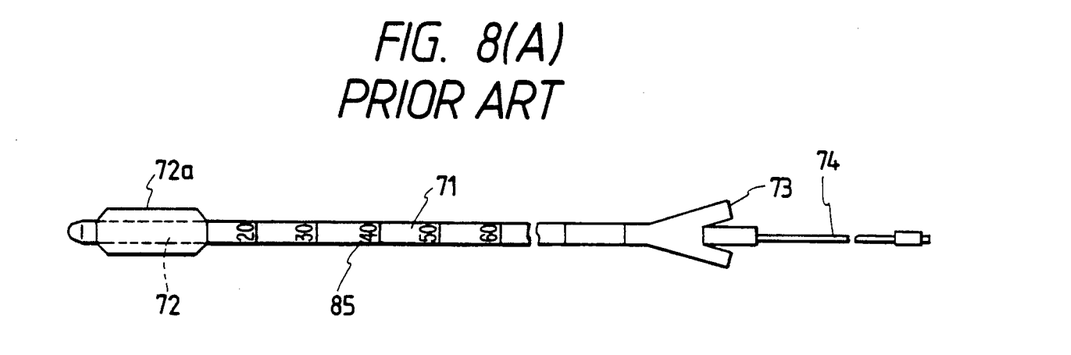
FIG. 8(A) is a front view of one example of a conventional electrode structure which is inserted into the body cavity.

FIG. 8(A) shows one example of a conventional high frequency hyperthermia device's electrode structure which is inserted into a body cavity.

The electrode structure, or an applicator comprising an electrode and a solution containing bag, comprises: a elongated flexible pipe 71; an electrode 72 built in one end portion of the flexible pipe 71; a cooling solution containing bag 72a combined suitably with the electrode 72; and a two-prongs-fork-shaped cooling solution circulating mouth 73 at the other end portion which is used to circulate a cooling solution to the solution containing bag 72a. The electrode structure further comprises: an electrode lead wire 74 led out of the pipe 71 so that the electrode 72 is connected to a high frequency electric source through it.

Figure 8B:
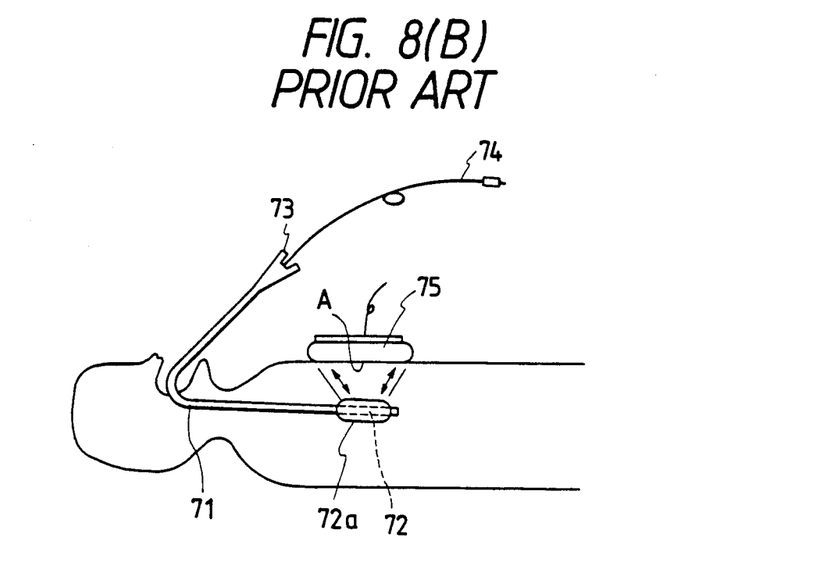
FIG. 8(B) is an explanatory diagram showing a medical treatment with the conventional electrode structure shown in FIG. 8(A)

As shown in FIG. 8(B), the applicator is inserted into the body cavity until the front electrode 72 (with the solution containing bag 72a) confronts with the cancer tissue. An ordinary portable applicator 75 (comprising an electrode and a solution containing bag) is placed on the skin of the organism (human body) A in such a manner that the cancer tissue is located between the electrode 72 and the portable applicator 75. Under this condition, a high frequency electric field is applied between the two electrodes, to heat the cancer tissue.

In the above-described electrode structure, the electrode is integral with the solution containing bag. Therefore, if the solution containing bag is broken, then the applicator itself can be no longer used. On the other hand, in order to treat the cancer tissue formed at a complicated part, such as the body cavity, of the body, it is necessary to provide a solution containing bag which is suitable for a part to be treated (such as the bottom of the body cavity, the tongue, or the rear side of the tongue). In order to satisfy this requirement, since in the conventional applicator, the electrode is integral with the solution containing bag, it is necessary to provide a variety of applicators different in structure. Furthermore, in the conventional electrode structure, the electrode is provided at the end of the flexible pipe, and accordingly it is difficult to fixedly hold the electrode which is inserted into the body cavity and confronted with the diseased part. In this case, heretofore, the tongue of the patient is utilized to fixedly hold the electrode. This method will cause the patient a pain, and at worst burn the tongue with the hot electrode.

Figure 9:
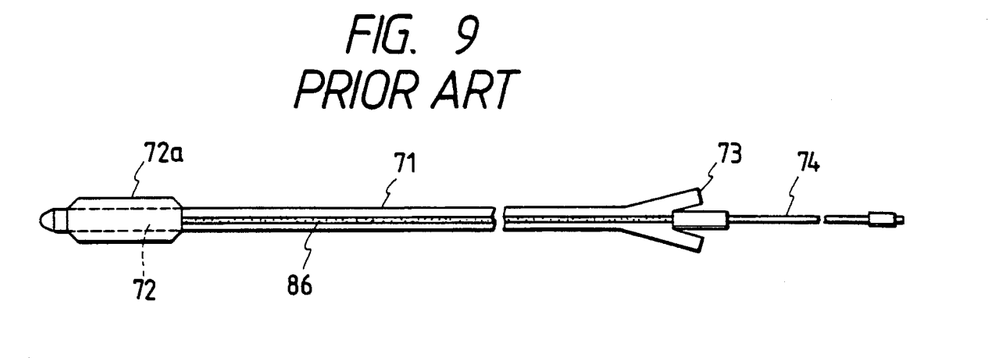
FIG. 9 is a front view of another example of the conventional electrode structure.

Furthermore, in the case where the diseased part is treated by heating it with the electrode structure, it is essential to allow the electrode to suitably confront with the diseased part (cancer tissue). However, since, in this case, the electrode is inserted into the body cavity, it is impossible to observe the electrode from outside; that is, it is impossible to determine whether or not the electrode is correctly confronted with the diseased part. Therefore, heretofore the following two methods are employed to detect the position of the electrode inserted into the body cavity: In the first method, as shown in FIG. 8(A), a measure 85 is provided for the pipe 71, so that, when the electrode is inserted into the body cavity, its depth is detected by reading the measure 85: that is, the first method is of a visual system. In the second method, as shown in FIG. 9, a line 86 is formed on the pipe 71 by coating it with an X-ray contrast medium, so that the position of the electrode 72 is detected through X-rays. That is, the second method is of an X-ray system.

Figure 10:
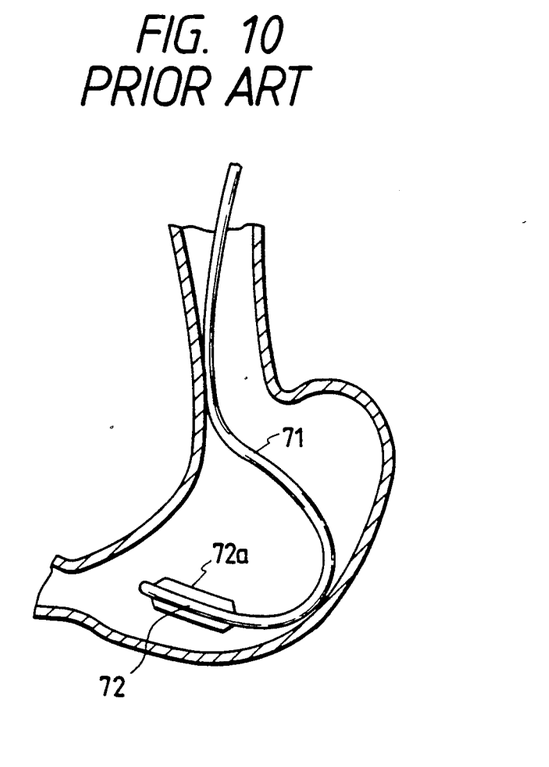
FIG. 10 is an explanatory diagram for a description of a medical treatment with the conventional electrode structure.

However, the two methods are disadvantageous in the following points: as shown in FIG. 10. That is, the first method suffers from the following difficulty: In the case where the body cavity has a bent part as in the case of the stomach, the pipe 71 inserted into it is bent there, and accordingly it is difficult to determine the depth of the electrode 72 correctly. In the case of the second method of X-ray system, the electrode 72 is inserted into the patient in the room where the X-ray device is installed (i.e., in the room which is different from the treating room, and the position of the electrode 72 is confirmed through X-rays. Under this condition, the patient is moved back to the treating room. This will cause the patient great pain.

SUMMARY OF THE INVENTION

Accordingly, an object of this invention is to eliminate the above-described difficulties accompanying a conventional electrode structure provided for a high frequency hyperthermia device.

More specifically, an object of the invention is to provide an electrode structure for a high frequency hyperthermia device in which a plurality of solution containing bags suitable for the diseased parts are provided for a single electrode, and the electrode in close contact with the diseased part is safely held in the body cavity.

Another object of the invention is to provide an electrode structure for a high frequency hyperthermia device in which the position of the electrode inserted into the body cavity can be determined readily and positively.

The foregoing objects and other objects of the invention have been achieved by the provision of the following electrode structures for a high frequency hyperthermia device:

In an electrode structure for a high frequency hyperthermia device, according to a first aspect of the invention, an electrode unit incorporating an electrode is provided at the front end portion of a supporting arm, and a cooling solution containing bag is detachably mounted on one side of the electrode unit.

In an electrode structure for a high frequency hyperthermia device, according to a second aspect of the invention, an electrode unit incorporating an electrode is provided at the front end portion of a supporting arm, and an insulated bag which is elastic so as to be inflated or deflated is provided on one side of the electrode unit.

In an electrode structure for a high frequency hyperthermia device, according to a third aspect of the invention, an electrode unit incorporating an electrode is provided at the front end portion of a supporting arm, and an insulated bag which is elastic so as to be inflated or deflated is provided on one side of the electrode unit, and a cooling solution containing bag is detachably provided on the other side of the electrode unit.

In an electrode structure for a high frequency hyperthermia device, according to a fourth aspect of the invention, an electrode and a cooling solution containing bag surround the electrode are provided at the front end of a flexible inserting tube, and a magnetic element is provided for the flexible inserting tube, for detecting the position of the electrode inserted into the body cavity.

In the electrode structure provided according to the first or third aspect of the invention, the electrode unit and the solution containing bag are detachably engaged with each other through detachably engaging means. For instance, engaging members are provided on the supporting arm so as to detachably hold the solution tubes extended from the solution containing bag, to fixedly secure the solution containing bag to the upper surface of the electrode unit. That is, the solution containing bag is detachably mounted on the electrode unit. Therefore, when the solution containing bag is broken by aging, the treatment can be performed merely by replacing the bag. For the same reason, a variety of solution containing bags can be provided separately according to the diseased parts in the oral cavity, and therefore the solution containing bag most suitable for treating the diseased part can be coupled to the electrode unit; that is, the diseased part can be most suitably treated.

In the electrode structure provided according to the second or third aspect of the invention, the insulated bag which is elastic so as to be inflated or deflated is provided on one side of the electrode unit. After the electrode is inserted into the oral cavity and confronted with the diseased part, the bag is inflated by an air supplying device connected through a tube thereto. As the bag is inflated, the surface of the bag is brought into contact with the mucous membrane of the oral cavity which is opposite to that in which the diseased part is located, whereby the electrode unit is abutted against the diseased part and is fixedly secured. In addition, the bag thus inflated provides a high insulation region behind the electrode unit, thus preventing the leakage of high frequency energy.

In the electrode structure according to the fourth aspect of the invention, the magnetic element (permanent magnet) is provided near the electrode. Therefore, the position of the electrode inserted into the body cavity can be readily detected by using a gauss meter. After the electrode is inserted, for instance, into the esophagus, the probe of the gauss meter is moved over the body along the esophagus. In this operation, the position of the magnetic element, and accordingly the position of the electrode can be confirmed from the deflection of the pointer of the gauss meter.

The nature, principle and utility of the invention will become more apparent from the following detailed description when read in conjunction with the accompanying drawings.

DETAILED DESCRIPTION OF THE INVENTION

Figure 1:
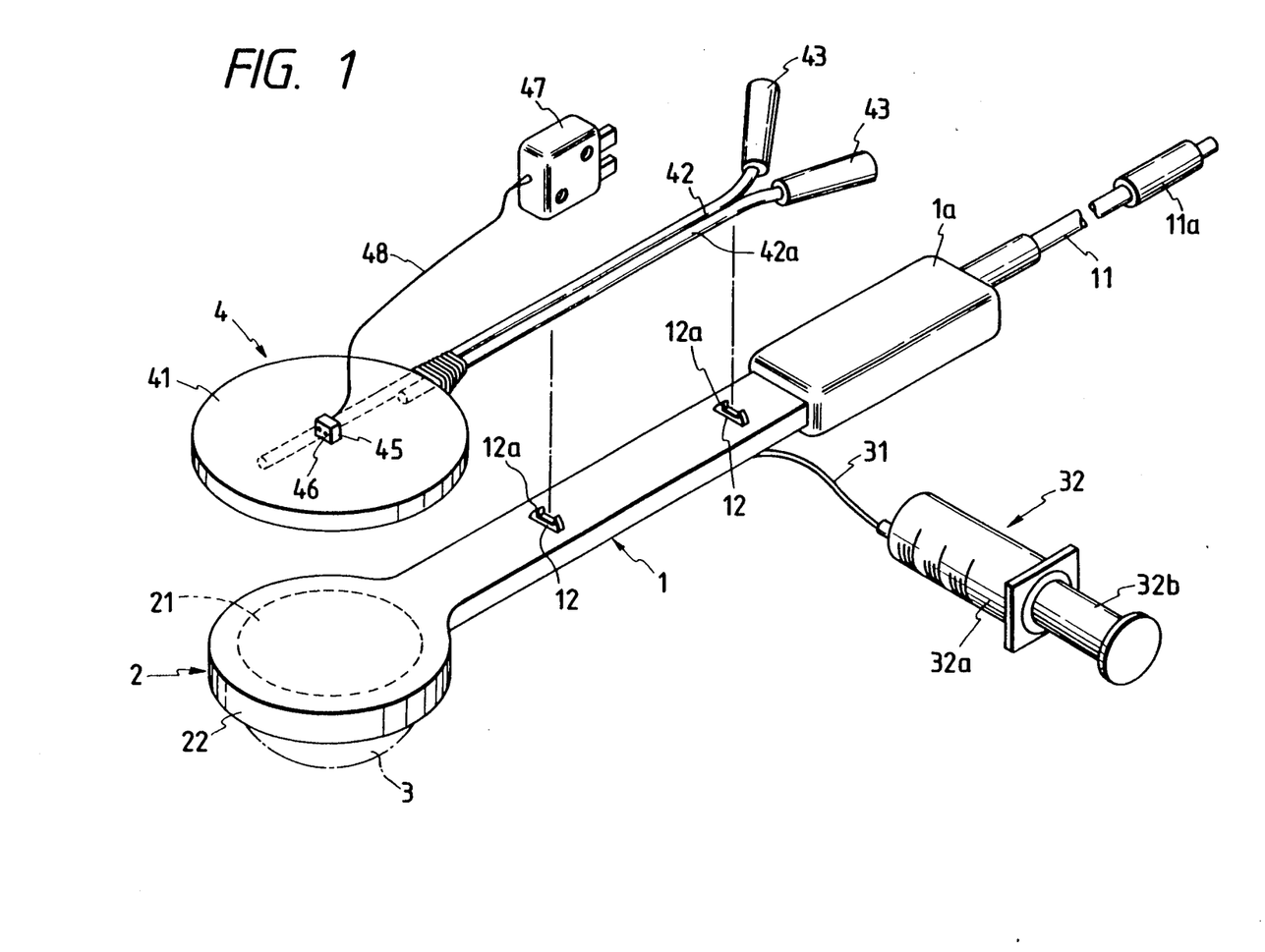
FIG. 1 is an exploded perspective view showing one example of an electrode structure for a high frequency hyperthermia device according to this invention.

A first example of an electrode structure for a high frequency hyperthermia device according to this invention, as shown in FIG. 1, comprises: an electrode unit 2 at the front end of an insulated support arm 1; an insulated bag 3 provided on the rear side of the electrode unit 2, the bag 3 being expandable; and a solution containing bag 4 detachably mounted on the upper surface of the electrode unit 2.

Figure 4:
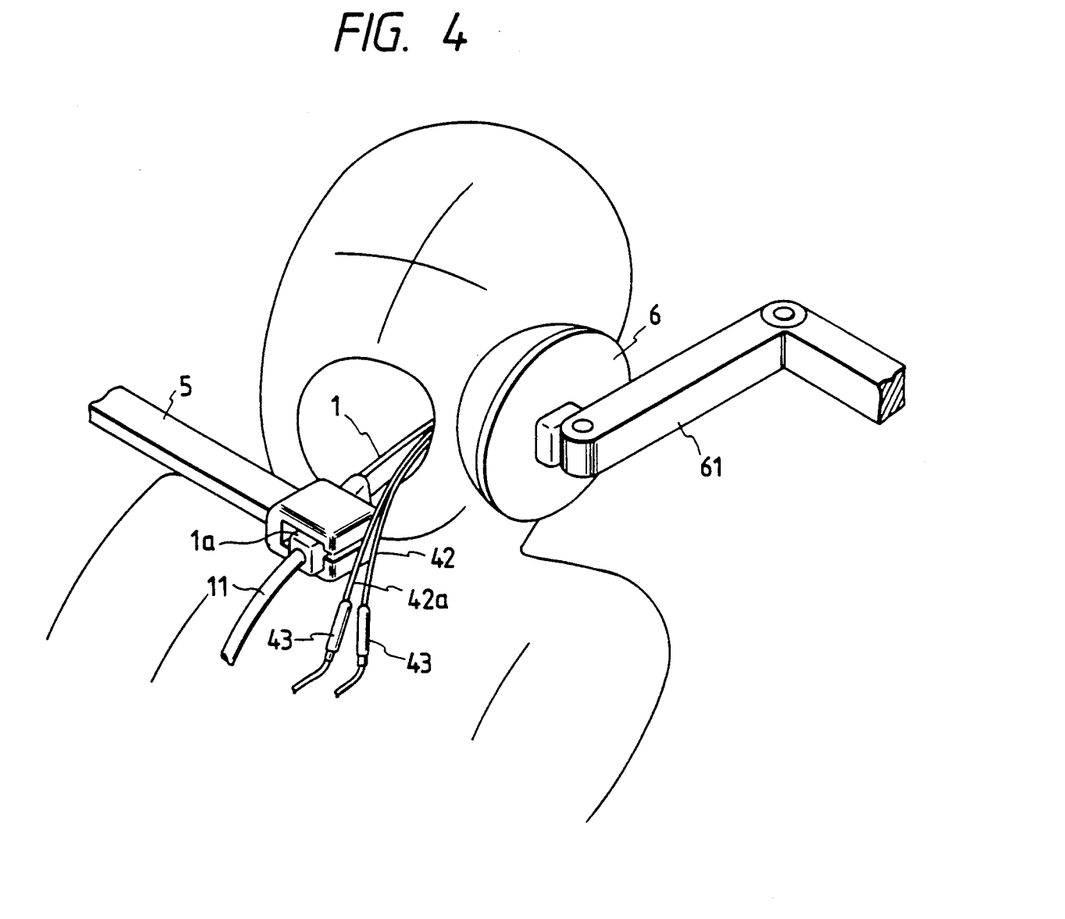
FIG. 4 is an explanatory diagram showing a medical treatment with the electrode structure according to the invention.

The insulated support arm 1 is a relatively flat pipe which is rectangular in section and open at both ends, and it is made of insulating material such as plastics. The support arm 1 has the electrode unit 2 at the front end. An electric cable 11 is built in the support arm 1 in such a manner that it is connected to an electrode 21 in the electrode unit 2. The support arm 1 has a base end part 1a at the other end which is larger than the other part and is fixedly held with a fixing arm 5 (as shown in FIG. 4) when the applicator is inserted into the oral cavity. The base end portion of the cable 11 is extended from the base end part 1a of the support arm 1, and is connected through a connector 11a to a high frequency voltage generating means (not shown). A plurality of engaging means 12 such as elastic pawls are formed on the upper surface of the support arm 1; in other words, the elastic pawls and the support arm are molded as one unit. The solution tubes 42 and 42a of the solution containing bag 4 (described later) are detachably engaged with the elastic pawls 12a.

The electrode unit 2 is made up of a disk-shaped electrode casing 22, and the electrode 21 sealingly built in the casing 22. The electrode 21 is made of an electrically conductive metal such as copper or aluminum, or an electrically conductive resin. The electrode 21 is connected to the cable 11, and then molded in the casing 22 with an insulating material such as silicon or latex.

Figure 2:
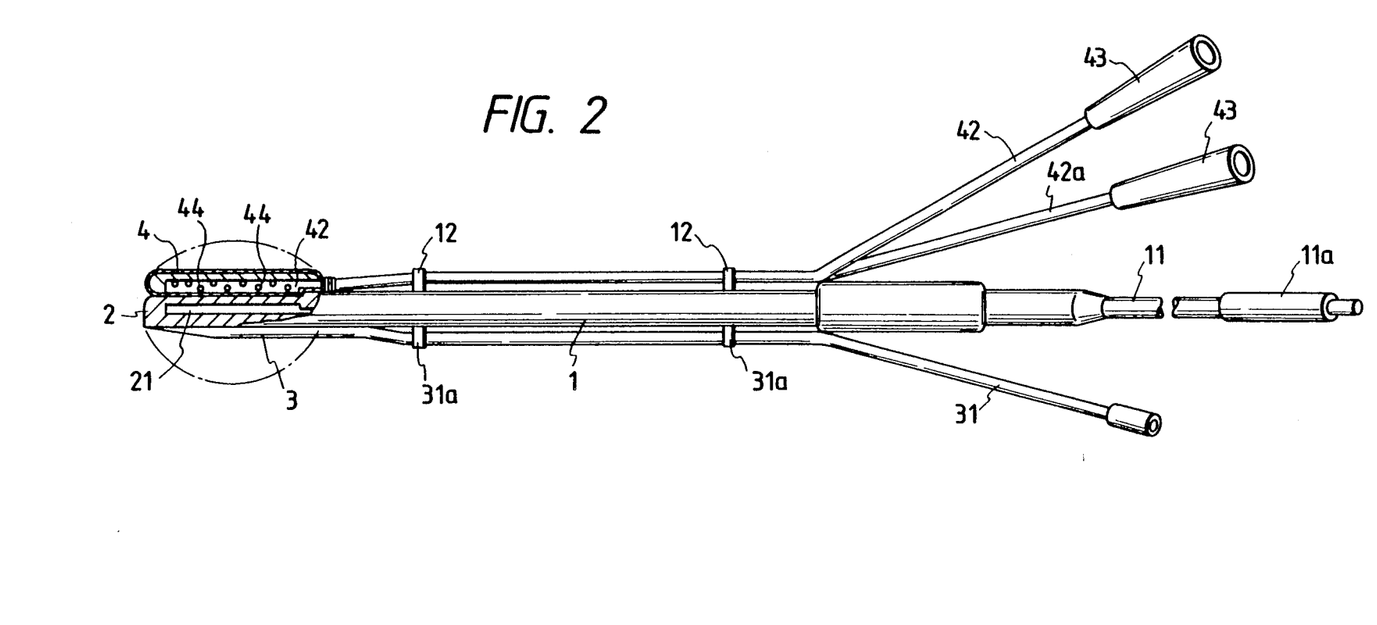
FIG. 2 is a side view of the electrode structure shown in FIG. 1.

The insulated bag 3 is provided on the lower surface (rear surface) of the electrode unit 2 (electrode casing 22). More specifically, the insulated bag 3 is coupled to the electrode unit 2 by securing its open end to the lower peripheral edge of the electrode unit 1. The insulated bag 3 is connected through an air tube 31 to an air supplying device 32, so that it is inflated or deflated by operating the latter 32. In the case of FIG. 1, the air supplying device 32 is made up of an air cylinder 32a and a piston rod 32b. The air tube 31 is fixedly secured to the lower surface of the support arm 1 with belts 31a or the like as shown in FIG. 2.

The solution containing bag 4 comprises a disk-shaped bag 41 made of a macromolecular material high in elasticity such as silicon or latex rubber. The aforementioned two cooling solution tubes 42 and 42a are inserted into the solution containing bag 4, and their free end portions are connected to connectors 43 and 43, respectively, which are connected to a cooling solution circulating device (not shown). Inside the bag 4, the end of the cooling solution tube 42 is closed as shown in FIG. 2, and the end portion has a plurality of pin holes 44 through which the cooling solution is supplied into the bag 4. The cooling solution in the bag is discharged through the other cooling solution tube 42a. The cooling solution tubes 42 and 42a are made of hard resin or the like in such a manner that they are integral except for the parts close to the connectors. The cooling solution tubes 42 and 42a thus combined are detachably engaged with the above-described engaging members 12 (elastic pawls 12a). A temperature sensor locking member 45 with two through-holes 46 and 46 is provided on the upper surface of the solution containing bag 4 at the center. The end portion of the lead wire of a sensor circuit 47 is inserted into one of the two through-holes 46, and then bent into the other through-hole 46, so that it is fixedly secured to the locking member 45.

Figure 3:
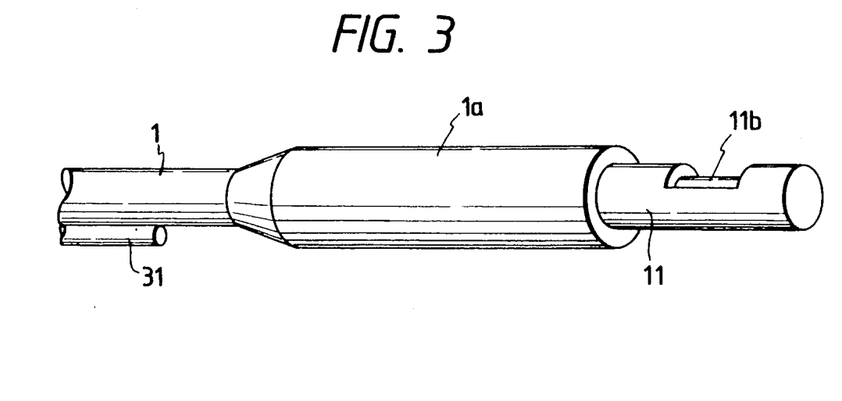
FIG. 3 is a perspective view showing another example of an electric cable employed in the electrode structure shown in FIG. 1.

FIG. 3 is a perspective view showing essential components of another example of the electric cable 11.

In the case of FIG. 1, the electric cable 11 is extended long from the base end of the support arm 1, and connected to the high frequency electric source. On the other hand, in the case of FIG. 3, the electric cable 11 is extended short from the support arm 1, and its base end portion is formed into a connector 11b. In this case, the support arm 1 and the connector 11b may be formed as one unit. Therefore, by forming a connector receiving means (not shown) on the fixing arm 5 which supports the support arm 1 when the electrode structure (applicator) is inserted into the oral cavity, supplying current and positioning the electrode can be carried out simultaneously.

With the electrode structure thus constructed, under normal conditions the cooling solution tubes 42 and 42a are fixedly held by the engaging members 12, and the solution containing bag 4 are held on the upper surface of the electrode unit 2. For instance when the solution containing bag 4 is broken by aging, it can be readily removed from the electrode unit 2 merely by disengaging the cooling solution tubes 42 and 42a from the engaging members 12; that is it can be readily replaced by a new one. In addition, for the same reason, in treating the diseased part by heating it, the solution containing bag on the electrode unit 2 can be readily replaced by one which is most suitable for the diseased part. Thus, the treatment of the diseased part can be most suitably achieved.

In treating the diseased part in the oral cavity by heating, as shown in FIG. 4, the support arm 1 is held with the fixing arm 5, and under this condition the electrode unit 2 (electrode 21) is inserted into the oral cavity until it is brought into contact with the diseased part. In this operation, the surface of the solution containing bag 4 on the electrode unit is brought into contact with the diseased part. And an ordinary portable applicator 6 supported by an arm 61 is placed on the skin of the body (the cheek) so that the diseased part is between the electrode unit 2 and the applicator. Under this condition, the air supplying means 32 is operated to supply the compressed air into the insulated bag 3, to inflate the latter 3. In this operation, as indicated by the phantom line in FIG. 2, the bag 3 is inflated in the opposite direction to the solution containing bag 4. That is, the insulated bag 3 thus inflated is brought into contact with the mucous membrane of the oral cavity which is opposed to the diseased part, while the electrode unit 2 is fixedly held in such a manner that it is abutted against the diseased part. Under this condition, a high frequency electric field is applied between the two electrodes, to treat the cancer tissue in the oral cavity by heating. The insulated bag 3 operates not only to cause the electrode unit 2 (electrode 21) to suitably abut against the diseased part, but also to provide a high insulation region behind the electrode 21, thereby to prevent the leakage of the high frequency energy.

In the above-described electrode structure, the support arm 1 is made up of an insulating material, and the electrode 21 is provided at the end of the support arm 1, is connected to the electric cable which is extended along or inside the support arm 1. However, the electrode structure may be modified as follows: The support arm 1 is made of a metal material such as a copper plate in such a manner that it has a circular electrode at the end. Alternatively, the cooling solution tubes 42 and 42a are accommodated in an arm which is detachably secured to the support arm 1 with screws or the like.

As was described above, in the electrode structure according to the invention, the electrode unit and the solution containing bag are separable from each other. Therefore, in the case where the solution containing bag is broken by aging, the treatment can be carried out merely by replacing the broken solution containing bag with a new one, with the results that the running cost is reduced, and the medical treatment is clean. Furthermore, in treating the diseased part, the solution containing bag most suitable for the diseased part can be selected, and combined with the electrode unit, with the results that the treatment is carried out correctly. In addition, with the electrode structure of the invention, after the electrode unit is confronted with the diseased part in the oral cavity, the insulated bag located behind the electrode unit is inflated, so that the electrode unit is abutted against the diseased part, while the bag thus inflated provides a high insulation region behind the electrode whereby the leakage of the high frequency energy is prevented.

Figure 5:
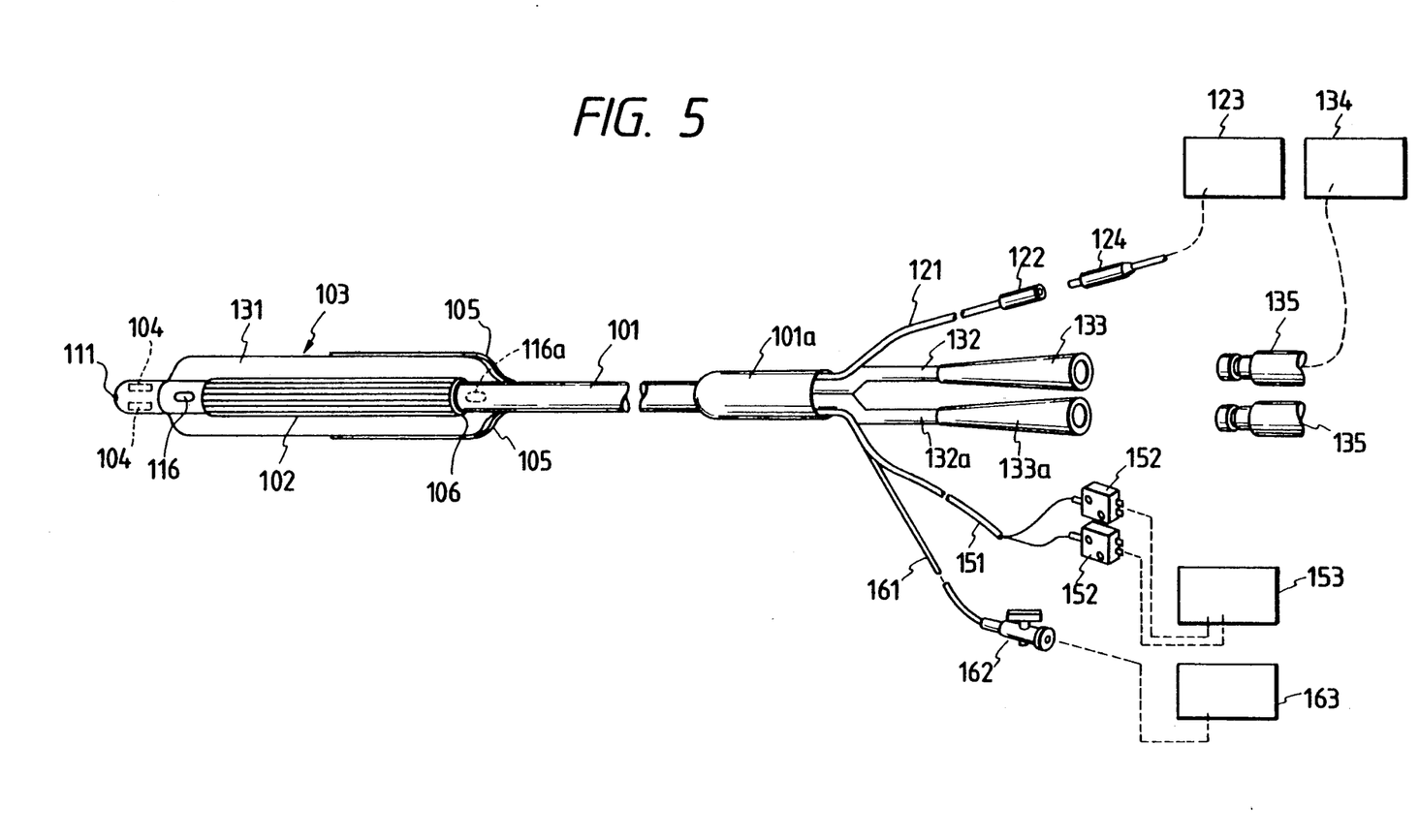
FIG. 5 is a perspective view, partly as a block diagram, showing another example of the electrode structure according to the invention.

Another example of the electrode structure for a high frequency hyperthermia device according to the invention, as shown in FIG. 5, comprises: a flexible inserting tube 101; and an electrode 102 and a solution containing bag 103 which are provided at one end of the inserting tube 101.

Figure 6:
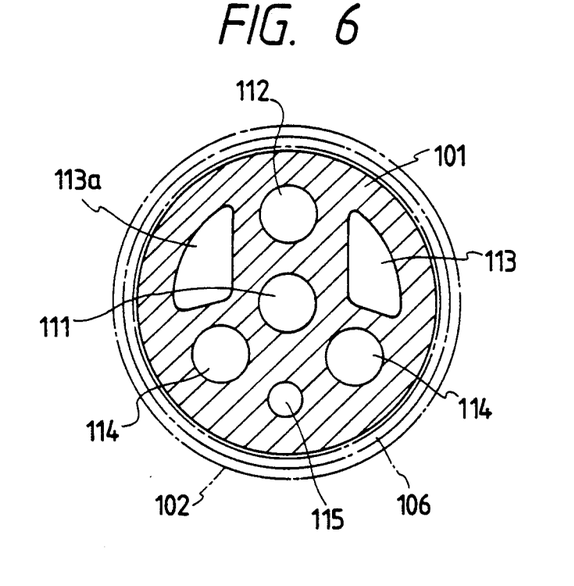
FIG. 6 is a sectional view of an inserting tube employed in the electrode structure shown in FIG. 5.

The inserting tube 101 is in the form of a cylinder having a predetermined length which is made of a macromolecular material or latex rubber which will not affect the organism. The inserting tube 101 has the electrode 102, the solution containing bag 103, and magnetic elements 104. As shown in FIG. 6, the inserting tube 101 has a guide wire inserting hole 111 formed along the central axis, and a cable inserting hole 112, solution tube inserting holes 113 and 113a, a temperature sensor lead wire inserting holes 114 and 114, and an air supplying tube inserting hole 115 formed around the guide wire inserting hole 111 in such a manner that those holes are extended in parallel with one another.

The guide wire inserting hole 111 is used when the electrode 102 is inserted into the body cavity. That is, a guide wire (not shown) which has been inserted into the body cavity is inserted into the hole 111, so that the electrode 102 (accordingly the inserting tube 101) be smoothly inserted into the body cavity. An electric cable 121 is inserted into the cable inserting hole 112. One end portion of the cable 121 is connected to the electrode 102, and the other end portion is extended from the base cylinder of the inserting tube and connected to a connector 122. The connector 122 is connected to a connector 124 of a high frequency voltage generating means 123, so that high frequency voltage is applied to the electrode 102. Cooling tubes 132 and 132a are inserted into the solution tube inserting holes 113 and 113a, respectively. One end of the cooling tube 132 is connected to the solution circulating inlet 116 of the inserting tube 101, and one end of the cooling tube 132 is connected to the solution circulating outlet 116a. The cooling tubes 132 and 132a extended out of the inserting tube 101 have connectors 133 and 133a at the other ends. The connectors 133 and 133a are connected to cooling tubes 135 of a cooling solution circulating device 134, so that the cooling solution is circulated into the solution containing bag 103.

Temperature measuring lead wires 151 are inserted into the temperature sensor lead wire inserting holes 114. End portions of the lead wires 151 are connected to temperature sensors 105 (described later), and the other end portions are extended out of the inserting tube 101 and connected to connectors 152, which are connected to a temperature measuring unit 153, so that the contact temperature of the solution containing bag with the surface of the organism is measured. An air supplying tube 161 is inserted into the air supplying tube inserting hole 115. One end portion of the air supplying tube 161 is connected to an electrode inflating bag 106 (described later), and the other end portion is extended out of the inserting tube 101 and connected to a two-way valve 162, which is connected to an air supplying unit 163, so that the electrode enlarging bag is inflated or deflated.

The electrode 102 is in the form of a cage-shaped cylinder made of thin wires, and it is fitted on the front end portion of the inserting tube 101. In other words, the front end portion of the inserting tube 101 is inserted into the cylindrical electrode 102, and both ends of the cylindrical electrode 102 are secured to the front end portion of the inserting tube 101. As shown in FIG. 6, the electrode inflating bag 106 is provided between the cylindrical electrode 102 and the inserting tube 101. The electrode inflating bag 106 is made of a material such as macromolecular material or latex rubber so that it is inflated or deflated by injection of air. Normally the bag is kept deflated. The bag 106 is inflated or deflated by operating the air supplying unit 163, so that the distance between the electrode 102 and the diseased part is changed (decreased or increased) thereby to effectively heat the diseased part.

The solution containing bag 103 is an elastic bag made of a material such as macromolecular material or latex rubber, and it is secured to the inserting tube 101 in such a manner that it surrounds the cylindrical electrode 102. Normally the bag 103 is kept deflated being substantially in contact with the electrode 102. As was described above, the inserting tube 101 has the solution circulating inlet 116 and the solution circulating outlet 116a on both sides of the electrode 102. As the cooling solution is supplied into the solution containing bag 103 by the cooling solution circulating device 134, the bag 103 is inflated so that the cooling solution is circulated through the electrode 102.

The temperature sensors 105 are sensor probes bonded to the upper and lower surfaces of the solution containing bag 103, and are used to measure the contact temperature of the surface of the organism and the solution containing bag 103.

One of the specific features of the electrode structure shown in FIG. 5 resides in that magnetic elements 104 for confirming the position of the electrode inserted are provided at the front end portion of the inserting tube 101.

In the case of FIG. 5, the magnetic elements 104 are permanent magnets which are buried in the front end portion of the inserting tube 102 near the electrode 102.

In the case where the above-described electrode structure for a high frequency hyperthermia device is used to treat the diseased part in the body cavity by heating it, first the inserting tube 101; i.e., the electrode 102 is inserted into the body cavity.

Figure 7:
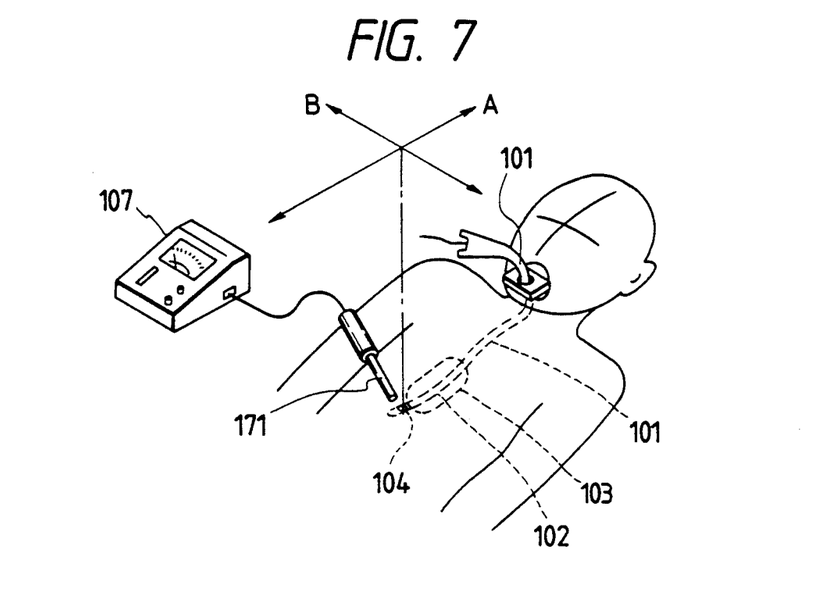
FIG. 7 is an explanatory diagram for a description of a method of determining the position of the electrode inserted into the cavity when the electrode structure shown in FIG. 5 is employed for treatment of the diseased part.

As shown in FIG. 7, the position of the electrode 102 inserted into the body cavity is detected by using a gauss meter. For instance in the case where the cancer tissue is in the esophagus, the electrode 102 (the inserting tube 101) is inserted through the oral cavity into the esophagus near to the diseased part (which has been confirmed through X-ray examination). Under this condition, the probe 171 of the gauss meter 107 is moved along the esophagus. During the movement of the probe 171, the pointer of the gauss meter will deflect maximumly when the probe comes to the position of the electrode 102. Thus, the position of the electrode 102 inserted into the body cavity can be detected readily. Hence, the electrode 102 can be positioned suitably with respect to the diseased part in the esophagus as follows: While the electrode 102 is being inserted, the probe 171 is moved along the esophagus so as to detect the position where the pointer of the gauss meter deflects maximumly at all times; that is, while the present position of the electrode is being detected, the electrode is inserted into the esophagus until it is positioned suitably with respect to the diseased part. More specifically, at the diseased position, the position of the electrode is adjusted so that the gauss meter indicates a maximum value in the direction of the arrow A (FIG. 7), and then the probe 171 is moved in the direction of the arrow B, to find the point where the gauss meter indicates a maximum value. The cross point of the maximum value point in the direction of the arrow B and the maximum value point in the direction of the arrow A is the electrode insertion point.

In the electrode structure shown in FIG. 5, the middle point of the electrode is about 50 mm from the connecting point of the solution tube 132; that is, the middle point of the electrode is slightly spaced from the magnetic elements 104. With the short distance therebetween taken into account, the position of the electrode can be correctly determined.

Owing to the provision of the magnetic elements 104, the position of the electrode can be readily detected merely by using the gauss meter, and the electrode can be positioned suitably with respect to the diseased part, with no pain given to the patient.

In the above-described electrode structure, the permanent magnets 104 are positioned in the front end portion of the inserting tube 101; however, it should be noted that the invention is not limited thereto or thereby. For instance, the permanent magnets may be provided near the electrode 102, or inside the inserting tube 101 at the middle of the electrode 102.

In the above-described electrode structure, the magnetic elements for detecting the position of the electrode inserted into the body cavity are provided for the inserting tube having the electrode at the end, as was described above. Hence, the position of the electrode inserted into the body cavity can be readily detected by using a gauss meter. Even when the inserting tube is slackened in the body cavity, the electrode can be positively located. Furthermore, the provision of the electrode structure of the invention, unlike the conventional one, eliminates the use of an X-ray device to locate the electrode, and makes it unnecessary to move the patient for confirmation of the position of the electrode inserted into the body cavity, thus relieving the patient of pain as much. In addition, even if the electrode is shifted in the body cavity during treatment, the present position of the electrode can be detected immediately. If necessary, during treatment the electrode can be moved to a position suitable for treating the diseased part, or to increase the heating region. Thus, the effects of the invention should be highly appreciated.

While there has been described in connection with the preferred embodiments of the invention, it will be obvious to those skilled in the art that various changes and modifications may be made therein without departing from the invention, and it is aimed, therefore, to cover in the appended claims all such changes and modifications as fall within the true spirit and scope of the invention.

What is claimed is:

1. An electrode structure for a high frequency hyperthermia device for nonsurgical insertion into a body cavity of a person, which comprises:
   a rigid supporting arm;
   an electrode unit incorporating an electrode which is provided at one end of said supporting arm; and
   a cooling solution containing bag detachably mounted on one side of said electrode unit;
   wherein said supporting arm is of a length to position said electrode unit in said body cavity from the exterior of said person.

2. An electrode structure for a high frequency hyperthermia device for nonsurgical insertion into a body cavity of a person according to claim 1, in which said supporting arm comprises:
   means for engaging solution tubes of said solution containing bag on a surface of said supporting arm.

3. An electrode structure for a high frequency hyperthermia device for nonsurgical insertion into a body cavity of a person, which comprises:
   a rigid supporting arm;
   an electrode unit incorporating an electrode which is provided at one end of said supporting arm; and
   an insulated bag which is elastic so as to be inflated or deflated, said insulated bag being provided on one side of said electrode unit;
   wherein said supporting arm is of a length to position said electrode unit in said body cavity from the exterior of said person.

4. An electrode structure for a high frequency hyperthermia device for nonsurgical insertion into a body cavity of a person, which comprises:
   a rigid supporting arm;
   an electrode unit incorporating an electrode which is provided at one end of said supporting arm;
   an insulated bag which is elastic so as to be inflated or deflated, said insulated bag being provided on one side of said electrode unit; and
   a cooling solution containing bag detachably mounted on other side of said electrode unit;
   wherein said supporting arm is of a length to position said electrode unit in said body cavity from the exterior of said person.

5. An electrode structure for a high frequency hyperthermia device for nonsurgical insertion into a body cavity of a person according to claim 4, in which said supporting arm comprises:
   means for engaging solution tubes of said solution containing bag on a surface of said supporting arm.

* * * * *